United States Patent
Kim et al.

(10) Patent No.: US 10,541,182 B2
(45) Date of Patent: Jan. 21, 2020

(54) METHOD OF INSPECTING SEMICONDUCTOR SUBSTRATE AND METHOD OF MANUFACTURING SEMICONDUCTOR DEVICE

(71) Applicant: Samsung Electronics Co., Ltd., Suwon-si (KR)

(72) Inventors: Yeon-tae Kim, Suwon-si (KR); Do-hyung Kim, Hwaseong-si (KR); Kwang-hyun Yang, Suwon-si (KR); Chang-yun Lee, Hwaseong-si (KR); Young-uk Choi, Seoul (KR); Kee-soo Park, Hwaseong-si (KR); Eun-sok Choi, Uiwang-si (KR)

(73) Assignee: SAMSUNG ELECTRONICS CO., LTD., Samsung-ro, Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 15/887,186

(22) Filed: Feb. 2, 2018

(65) Prior Publication Data

US 2019/0096773 A1 Mar. 28, 2019

(30) Foreign Application Priority Data

Sep. 28, 2017 (KR) .................. 10-2017-0126349

(51) Int. Cl.
| | |
|---|---|
| *G01N 21/95* | (2006.01) |
| *G01N 21/88* | (2006.01) |
| *H01L 21/66* | (2006.01) |
| *H01L 21/687* | (2006.01) |
| *G01B 11/24* | (2006.01) |
| *G01B 11/06* | (2006.01) |
| *G01N 21/55* | (2014.01) |
| *H01L 21/67* | (2006.01) |

(52) U.S. Cl.
CPC ........ *H01L 22/20* (2013.01); *H01L 21/67253* (2013.01); *H01L 21/67265* (2013.01); *H01L 21/68785* (2013.01)

(58) Field of Classification Search
CPC ......... H01L 22/26; H01L 22/12; B24B 49/04; B24B 37/005
See application file for complete search history.

(56) References Cited

U.S. PATENT DOCUMENTS

| | | |
|---|---|---|
| 6,099,596 A | 8/2000 | Li et al. |
| 6,950,774 B2 | 9/2005 | Donald |

(Continued)

FOREIGN PATENT DOCUMENTS

| | | |
|---|---|---|
| JP | H09-172047 A | 6/1997 |
| JP | 2007-127566 A | 5/2007 |

(Continued)

*Primary Examiner* — Brian Turner
(74) *Attorney, Agent, or Firm* — Muir Patent Law, PLLC

(57) ABSTRACT

A method of inspecting a semiconductor substrate includes measuring light intensity of light reflected on the rotating semiconductor substrate, analyzing a frequency distribution of the measured light intensity, and determining a state of the semiconductor substrate by using the frequency distribution. The analyzing of the frequency distribution of the measured light intensity includes extracting a plurality of frequency components corresponding respectively to a plurality of frequencies from the measured light intensity.

17 Claims, 16 Drawing Sheets

(56) References Cited

U.S. PATENT DOCUMENTS

| | | |
|---|---|---|
| 8,203,705 B2 | 6/2012 | Ooyama et al. |
| 9,354,047 B2 | 5/2016 | Kannaka et al. |
| 9,607,389 B2 | 3/2017 | Kodama |
| 9,627,239 B2 | 4/2017 | Kwon |
| 2015/0147829 A1* | 5/2015 | Benvegnu ............... H01L 22/26 438/8 |
| 2015/0192527 A1* | 7/2015 | Barak .................... H01L 22/12 356/237.6 |
| 2017/0219496 A1 | 8/2017 | Durand De Gevigney et al. |

FOREIGN PATENT DOCUMENTS

| | | |
|---|---|---|
| JP | 5025545 B2 | 6/2012 |
| KR | 10-2017-0066366 | 6/2017 |

* cited by examiner

METHOD OF INSPECTING SEMICONDUCTOR SUBSTRATE AND METHOD OF MANUFACTURING SEMICONDUCTOR DEVICE

CROSS-REFERENCE TO RELATED APPLICATION

This application claims the benefit of priority under 35 U.S.C. § 119 to Korean Patent Application No. 10-2017-0126349, filed on Sep. 28, 2017, in the Korean Intellectual Property Office, the disclosure of which is incorporated herein in its entirety by reference.

BACKGROUND

This disclosure relates to a method of inspecting a semiconductor substrate and a method of manufacturing a semiconductor device using the inspection method, and more particularly, to a method of inspecting a state of a rotating semiconductor substrate and a method of manufacturing a semiconductor device using the inspection method.

To process a semiconductor substrate, the semiconductor substrate may be fixed to a substrate holder (e.g., a susceptor) located in a chamber. In this case, the semiconductor substrate may be fixed in a misaligned state to the substrate holder or the fixed semiconductor substrate may move relative to the substrate holder during a processing process. Thus, the semiconductor substrate may be processed in an unintended manner, or an unintended temperature gradient may be caused to the semiconductor substrate during the processing of the semiconductor substrate, thereby resulting in damage to the semiconductor substrate. Therefore, there is an increasing need to inspect states (e.g., misalignment, inclination, and warpage) of semiconductor substrates.

SUMMARY

The disclosed embodiments provide a method of determining a state of a rotating semiconductor substrate in real-time without using an additional light source.

Aspects of the inventive concept should not be limited by the above description, and other unmentioned aspects will be clearly understood by one of ordinary skill in the art from example embodiments described herein.

According to an aspect, there is provided a method of inspecting a semiconductor substrate. The method includes measuring light intensity of light reflected on the semiconductor substrate while the semiconductor substrate rotates, analyzing a frequency distribution of the measured light intensity, and determining a state of the semiconductor substrate based on the frequency distribution. The analyzing of the frequency distribution of the measured light intensity includes extracting a plurality of frequency components corresponding respectively to a plurality of frequencies from the measured light intensity.

According to another aspect, there is provided a method of inspecting a semiconductor substrate. The method includes measuring light intensity of light reflected on the semiconductor substrate while the semiconductor substrate rotates, analyzing a frequency distribution of the measured light intensity, and determining a state of the semiconductor substrate based on the frequency distribution of the light intensity. The analyzing of the frequency distribution of the light intensity includes normalizing the frequency distribution of the light intensity.

According to another aspect, there is provided a method of manufacturing a semiconductor device. The method includes setting a processing environment of a semiconductor substrate, processing the semiconductor substrate according to the processing environment, inspecting the semiconductor substrate in real-time to determine a state of the semiconductor substrate, and determining whether the processing of the semiconductor substrate is to be continued based on the determined state of the semiconductor substrate. The inspection the semiconductor substrate in real-time includes measuring light intensity of light reflected on the semiconductor substrate while the semiconductor substrate rotates, calculating a frequency distribution of the measured light intensity, and determining the state of the semiconductor substrate by using the frequency distribution of the light intensity. The calculation of the frequency distribution of the measured light intensity includes extracting a plurality of frequency components corresponding respectively to a plurality of frequencies from the measured light intensity.

BRIEF DESCRIPTION OF THE DRAWINGS

Embodiments will be more clearly understood from the following detailed description taken in conjunction with the accompanying drawings in which.

Figure 1:
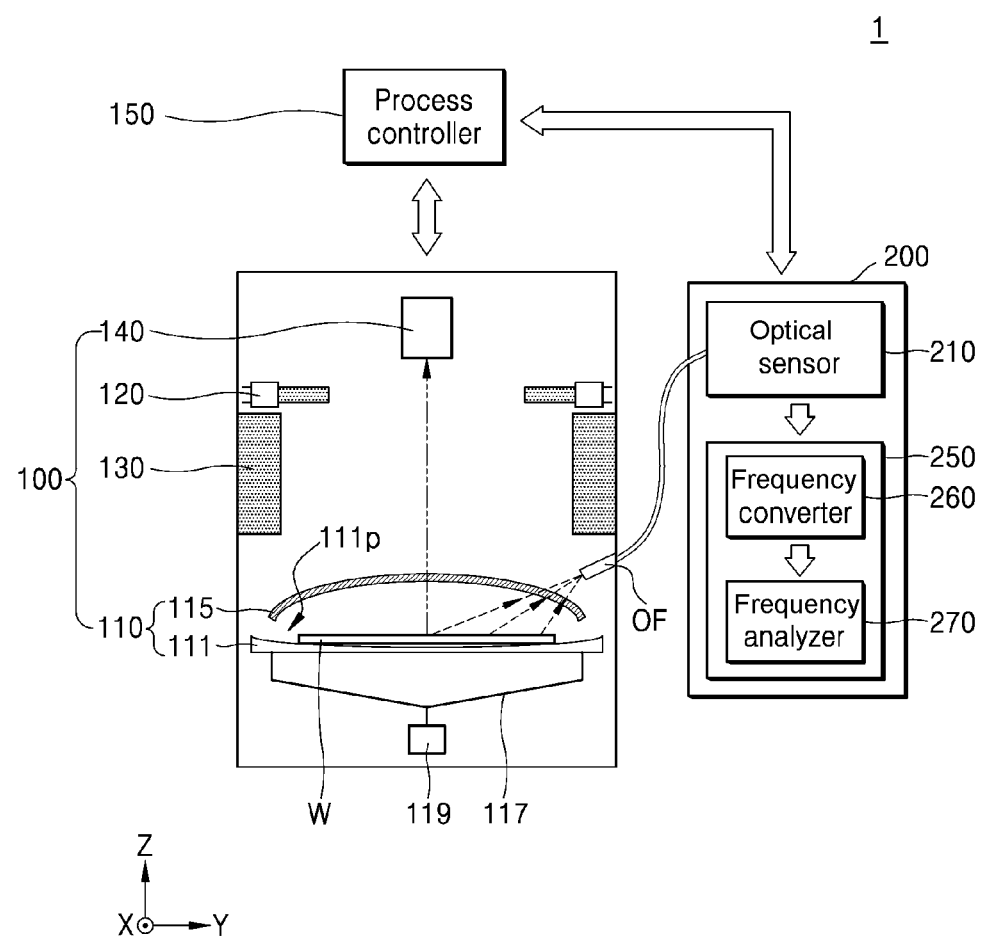
FIG. 1 is a cross-sectional view of a method of inspecting a semiconductor substrate and a method of manufacturing a semiconductor device using the inspection method, according to some exemplary embodiments.

DETAILED DESCRIPTION OF THE EMBODIMENTS,

FIG. 1 is a cross-sectional view of a method of inspecting a semiconductor substrate W according to some embodiments and a method of manufacturing a semiconductor device using the inspection method. FIG. 1 illustrates a substrate processing system 1 including a process chamber 100, a process controller 150, and a substrate state inspection device 200.

To manufacture the semiconductor device, a predetermined processing operation may be performed on the semiconductor substrate W in the process chamber 100. In some embodiments, the semiconductor substrate W may include a semiconductor, such as silicon (Si) or germanium (Ge), or a compound semiconductor, such as silicon germanium (SiGe), silicon carbide (SiC), gallium arsenide (GaAs), indium arsenide (InAs), or indium phosphide (InP). In some embodiments, the semiconductor substrate W may have a silicon-on-insulator (SOI) structure. In some embodiments, the semiconductor substrate W may include a conductive region, for example, a doped well or a doped structure. Although various embodiments are described below with reference to "semiconductor substrates," these embodiments may have a wider range of applicability. For example, the embodiments may be applied to arbitrary cases in which it is necessary to determine whether given semiconductor substrates W or workpieces have been appropriately aligned and planarly disposed (e.g., whether inclination or warpages have occurred) in a processing environment.

According to some embodiments, a deposition process of forming predetermined films may be performed on the semiconductor substrate W. According to some embodiments, the predetermined films may be formed on the semiconductor substrate W by using an atomic layer deposition (ALD) process, a chemical vapor deposition (CVD) process, a plasma-enhanced CVD (PECVD) process, a physical vapor deposition (PVD) process, and/or a reactive pulsed laser deposition (RPLD) process. According to some embodiments, the predetermined films may be formed on the semiconductor substrate W by using a molecular beam epitaxy (MBE) process or a metal organic CVD (MOCVD) process. According to some embodiments, the predetermined films may be formed on the semiconductor substrate W by using a direct-current (DC) magnetron sputtering process using krypton (Kr) as a sputtering gas.

According to some embodiments, the method of manufacturing the semiconductor device may include etching the predetermined films formed on the semiconductor substrate W to form a pattern. According to some embodiments, the predetermined films deposited on the semiconductor substrate W may be etched by using a dry etching process. According to some embodiments, the predetermined films deposited on the semiconductor substrate W may be etched by using a process, such as a plasma etching process, a reactive ion etching (RIE) process, a deep RIE (DRIE) process, an ion beam etching (IBE) process, or an argon (Ar) milling process. According to some embodiments, the predetermined films formed on the semiconductor substrate W may be etched by using a wet etching process. According to some embodiments, the predetermined films formed on the semiconductor substrate W may be etched by using a wet etching process using, as an etchant gas, at least one selected from the group consisting of $Cl_2$, HCl, $CHF_3$, $CH_2F_2$, $CH_3F$, $H_2$, $BCL_3$, $SiCl_4$, $Br_2$, HBr, $NF_3$, $CF_4$, $C_2F_6$, $C_4F_8$, $SF_6$, $O_2$, $SO_2$, and COS. According to some embodiments, the predetermined films formed on the semiconductor substrate W may be etched by using an atomic layer etching (ALE) process. According to some embodiments, additional films may be further formed on the pattern formed on the semiconductor substrate W by using substantially the same processes as the above-described processes of forming the predetermined films.

According to some embodiments, a planarization process, such as a chemical mechanical polishing (CMP) process and/or an etchback process, an ion implantation process, and a photolithography process may be performed.

The process chamber 100 may include a susceptor 110, a lamp 120, a reflector 130, and a temperature sensor 140.

Directions that are parallel to a top surface of a normally disposed semiconductor substrate W and intersect each other perpendicularly may be referred to as a first direction X and a second direction Y. Also, a direction that is substantially perpendicular to the top surface of the semiconductor substrate W may be referred to as a third direction Z. Here, when the semiconductor substrate W is normally disposed, it may be inferred that the semiconductor substrate W is suitably disposed to perform a process. For example, the normal disposition of the semiconductor substrate W may refer to a state in which misalignment, inclination, or warpage does not occur in the semiconductor substrate W, but the inventive concept is not limited thereto. The first direction X and the second direction Y may be substantially perpendicular to the third direction Z. A direction indicated by an arrow in FIG. 1 and a direction opposite thereto may be referred to as the same direction. Terms such as "same" and "equal," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to emphasize this meaning, unless the context or other statements indicate otherwise. For example, items described as "substantially the same" or "substantially equal" may be exactly the same or equal, or may be the same or equal within acceptable variations that may occur, for example, due to manufacturing processes. Definitions of the above-described directions may be the same in the following drawings.

The susceptor 110 may include a substrate support unit 111 and a susceptor window 115, and the substrate support unit 111 may include a substrate pocket 111P in which the semiconductor substrate W may be mounted. According to some embodiments, the susceptor 110 may rotate the mounted semiconductor substrate W. The susceptor 110 may be mounted on a support structure 117, which is operably connected to a motor 119. The motor 119 may drive the support structure 117 configured to rotate the susceptor 110 in which the semiconductor substrate W is mounted. According to some embodiments, the susceptor 110 may rotate about an axis that passes through the center of the susceptor 110 and is substantially parallel to the third direction Z. According to some embodiments, the substrate pocket 111P may have such a size as to contain a specific type of semiconductor substrate W, for example, an about 200-mm or 300-mm semiconductor substrate. However, the inventive concept is not limited to the present embodiment and may be applied to arbitrary configurations and shapes capable of rotating at least one semiconductor substrate W.

The semiconductor substrate W may be isolated from the outside of the susceptor 110 by the substrate support unit 111 and the susceptor window 115 and put in a predetermined process atmosphere. The susceptor window 115 may be transparent with respect to light emitted by the lamp 120. Thus, the light emitted by the lamp 120 may be transmitted through the susceptor window 115 and reach the semiconductor substrate W.

The lamp 120 may generate thermal energy as light to set a processing environment of the semiconductor substrate W. The lamp 120 may be located above the semiconductor substrate W and may transmit light to the semiconductor substrate W, but the inventive concept is not limited thereto. The lamp 120 may adjust temperatures of the inside of the process chamber 100, the semiconductor substrate W, and the susceptor 110. The lamp 120 may heat the semiconductor substrate W and the process chamber 100 so that the temperatures of the semiconductor substrate W and the inside of the process chamber 100 may reach predetermined temperatures required for processes. The reflector 130 may be configured to reflect light, which travels from the lamp 120 to the reflector 130, in a direction toward the semiconductor substrate W. However, the inventive concept is not limited thereto, and the reflector 130 may be omitted in some embodiments.

According to some embodiments, the temperature sensor 140 may measure a temperature of the semiconductor substrate W or the susceptor 110. According to some embodiments, the temperature of the semiconductor substrate W or the susceptor 110 may be measured with black-body radiation light emitted by the temperature sensor 140, the semiconductor substrate W, or the susceptor 110. The temperature sensor 140 may correspond to an infrared (IR) sensor, but the inventive concept is not limited thereto.

The process controller 150 may control the performance and/or the selection of the processing for the semiconductor substrate W. The process controller 150 may control the processing environment of the semiconductor substrate W. The process controller 150 may be a computing device, such as a workstation computer, a desktop computer, a laptop computer, or a tablet computer. The process controller 150 may include software configured to receive feedback on the processing of the semiconductor substrate W, receive measurement data, and adjust processes. The process controller 150 may be a simple controller or a more complex processor (such as a microprocessor, a CPU, a GPU, etc.) or processors configured by software, or may be dedicated hardware or firmware. For example, the process controller 150 may be embodied as a computer, which may be a general purpose computer or application-specific hardware, such as, for example, a digital signal processor (DSP), a field-programmable gate array (FPGA), an application specific integrated circuit (ASIC). According to some embodiments, the process controller 150 may, for example, control emission of the lamp 120 and adjust a temperature of the semiconductor substrate W or the susceptor 110. For example, the process controller 150 may change the light intensity of the light emitted by the lamp 120 and thereby cause a change in temperature of the semiconductor substrate W or the susceptor 110. According to some embodiments, the process controller 150 may adjust, for example, an atmosphere of the susceptor 110 and a rotation speed of the semiconductor substrate W, but the inventive concept is not limited thereto.

The substrate state inspection device 200 may include an optical sensor 210 and an inspection processor 250. The substrate state inspection device 200 may be combined with the process chamber 100 by an optical fiber OF. However, the inventive concept is not limited thereto, and the optical sensor 210 may be directly combined with the process chamber 100.

According to some embodiments, the optical fiber OF may receive light emitted by the lamp 120, radiation light emitted by the semiconductor substrate W, reflected light on the semiconductor substrate W (e.g., light that is emitted by the lamp 120 and reflected on the surface of the semiconductor substrate W), and light reflected on other components of the process chamber 100. According to some embodiments, the optical fiber OF may mainly receive light reflected on the top surface of the semiconductor substrate W. According to some embodiments, although the optical fiber OF receives light reflected on a portion of the top surface of the semiconductor substrate W, as the semiconductor substrate W rotates, the optical fiber OF may receive light reflected on a substantially large portion of the top surface of the semiconductor substrate W. However, the inventive concept is not limited thereto, and the optical fiber OF may receive light reflected on edge portions of the semiconductor substrate W. The edge portions of the semiconductor substrate W may refer to portions adjacent to the circumference of a substantially disc shape of the semiconductor substrate W. For example, edge portions of the semiconductor substrate W may include top and side surface portions at the perimeter of the semiconductor substrate W.

According to some embodiments, the optical fiber OF may be combined with the optical sensor 210 of the substrate state inspection device 200. The optical fiber OF may transmit the received light to the optical sensor 210. The optical sensor 210 may measure light intensity of light reflected on the top surface of the rotating semiconductor substrate W. The optical sensor 210 may provide a signal corresponding to the measured light intensity to the inspection processor 250.

The inspection processor 250 may include a frequency converter 260 and a frequency analyzer 270. The frequency converter 260 may convert data about light intensity measured by the optical sensor 210 in a time domain into data about light intensity in a frequency domain. The frequency converter 260 may perform a Fourier transform on the light intensity in the time domain. The Fourier transform of the frequency converter 260 will be described in further detail below with reference to FIG. 3. The inspection processor 250 may comprise a computer including a processor (such as a microprocessor, a CPU, a GPU, etc.) or processors configured by software, or may be dedicated hardware or firmware. For example, the inspection processor 250 may be a general purpose computer or application-specific hardware, such as, for example, a digital signal processor (DSP), a field-programmable gate array (FPGA), an application specific integrated circuit (ASIC). The frequency converter 260 and frequency analyzer 270 may be separate and distinct hardware elements of the inspection processor 250 or may be software modules that configure the inspection processor 250.

The frequency analyzer 270 may analyze frequency-converted data. For example, the frequency analyser 270 may receive data converted by the frequency converter 260, and analyse the received frequency-converted data. The analysis performed by the frequency analyzer 270 will be described below with reference to FIG. 6.

According to some embodiments, the inspection processor 250 may compare physical properties of the semiconductor substrate W with reference values or critical values based on the analyzed data. According to some embodiments, the inspection processor 250 may compare alignment of the semiconductor substrate W, an inclination of the top surface of the semiconductor substrate W, warpage of the semiconductor substrate W, thicknesses of films deposited on the semiconductor substrate W, and critical dimensions (CDs) of patterns formed on the semiconductor substrate W with reference values or critical values. According to some embodiments, the inspection processor 250 may analyze measurement data by looking up the measurement data or comparing the measurement data with the existing on-line/off-line data. The on-line/off-line data may be the reference values or critical values. The measurement data and the on-line/off-line data each may be stored in databases or other memory devices, and the inspection processor 250 may retrieve the stored data for analysis and/or comparison. The inspection processor 250 may analyze the received measurement data and generate one or more feedback signals that the inspection processor 250 transmits to the process controller 150.

Feedback on the processing of the semiconductor substrate W in response to a feedback signal may affect various parameters used for performing and/or selecting the process of processing the semiconductor substrate W. According to some embodiments, the process controller 150 may adjust at least one process parameter or select a process set out of a plurality of process sets by using the analyzed measurement data. Examples of the process parameters may include a temperature, a pressure, an atmosphere, a luminance, and a duration time, but the inventive concept is not limited thereto.

Figure 2:
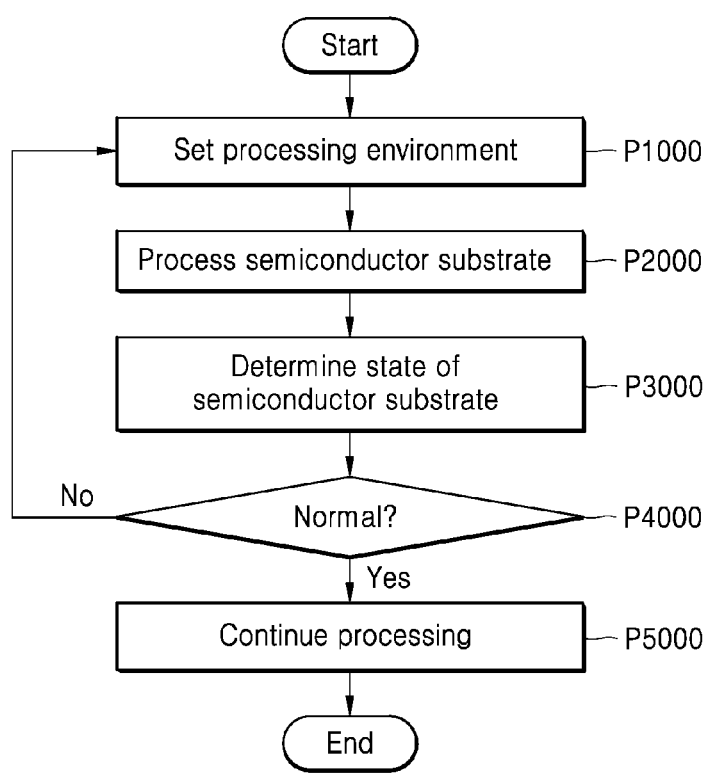
FIG. 2 is a flowchart of a method of manufacturing a semiconductor device using a method of inspecting a semiconductor substrate, according to some exemplary embodiments.

FIG. 2 is a flowchart of a method of manufacturing a semiconductor device according to some embodiments.

Referring to FIGS. 1 and 2, in process P1000, a process environment of the process chamber 100 may be set. According to some embodiments, the setting of the process environment may include selecting one or more sets out of a plurality of processing sets, which may be executed. According to some embodiments, the setting of the process environment may include setting one or more of a temperature, an atmosphere, a pressure, and a luminance in the process chamber 100. According to some embodiments, the setting of the process environment may include mounting the semiconductor substrate W on the susceptor 110. According to some embodiments, the setting of the process environment may include aligning the semiconductor substrate W with the susceptor 110. In some example embodiments, the setting or establishing of the process environment may include mounting the semiconductor substrate W on the susceptor 110, aligning the semiconductor substrate W with the susceptor 110, and setting one or more of a temperature, an atmosphere, a pressure, and a luminance in the process chamber 100.

Subsequently, in process P2000, the semiconductor substrate W may be processed. According to some embodiments, the processing of the semiconductor substrate W may include one or more of a process of forming an oxide film on the semiconductor substrate W, a photolithography process, a process of depositing predetermined films on the semiconductor substrate W, a process of etching the predetermined films formed on the semiconductor substrate W and/or the semiconductor substrate W, a process of forming an impurity region in the semiconductor substrate W, and a process of forming a conductive interconnection and a via in the semiconductor substrate W, but the inventive concept is not limited thereto.

Subsequently, in process P3000, the substrate state inspection device 200 may inspect a state of the semiconductor substrate W. According to some embodiments, the inspection of the state of semiconductor substrate W may include inspecting a state of a rotating semiconductor substrate W. According to some embodiments, the inspection of the state of the semiconductor substrate W may be performed in real-time simultaneously with the processing of the semiconductor substrate W. According to some embodiments, the inspection of the state of the semiconductor substrate W may include inspecting at least one of the misalignment, inclination, and warpage of the semiconductor substrate W, the thickness of the layer deposited on the semiconductor substrate W and the critical dimensions (CD) of the pattern formed on the semiconductor substrate W. For example, when inspecting the semiconductor substrate W to determine the state of the semiconductor substrate W, the substrate state inspection device 200 may inspect the semiconductor substrate W to determine whether there is a misalignment of the semiconductor substrate W and if so, calculate a measurement of the misalignment; determine whether there is an inclination of the semiconductor substrate W relative to a horizontal plane and, if so, calculate a measure of the inclination; determine whether there is warpage of the semiconductor substrate W and, if so, calculate a measure of the warpage; and calculate measurements of the thickness of the layer deposited on the semiconductor substrate W and/or the CD of the pattern formed on the semiconductor substrate W.

Thereafter, in process P4000, the substrate state inspection device 200 may determine whether the state of the semiconductor substrate W is normal. According to some embodiments, in process P4000, the determination of whether the state of the semiconductor substrate W is normal may include determining whether the misalignment, inclination, or warpage of the semiconductor substrate W has exceeded predetermined reference values or critical values. According to some embodiments, if the state of the semiconductor substrate W is determined as abnormal in process P4000, the process may return to P1000 and reset the semiconductor substrate W and the process environment of the process chamber 100. According to some embodiments, if the state of the semiconductor substrate W is determined as normal in process P4000, the semiconductor substrate W may be continuously processed. According to some embodiments, if it is determined in process P5000 that predetermined films are sufficiently deposited on the semiconductor substrate W, subsequent processes of providing a semiconductor device to the semiconductor substrate W may be performed.

However, the inventive concept is not limited to the above-described embodiments. According to some embodiments, in process P4000, the inspection processor 250 may determine a progress of the processing of the semiconductor substrate W. For example, in process P4000, the substrate state inspection device 200 may inspect the semiconductor substrate W and calculate measurements of the thickness of the layer deposited on the semiconductor substrate W and/or the CD of the pattern formed on the semiconductor substrate W. According to some embodiments, in process P5000, it may be determined whether the predetermined films have sufficiently been deposited on the semiconductor substrate W. According to some embodiments, if it is determined in process P5000 that the predetermined films have not sufficiently been deposited on the semiconductor substrate W, predetermined films may be continuously deposited. For example, if the predetermined films have not sufficiently been deposited on the semiconductor substrate W, the process may return to process P2000, as discussed above.

Figure 3:
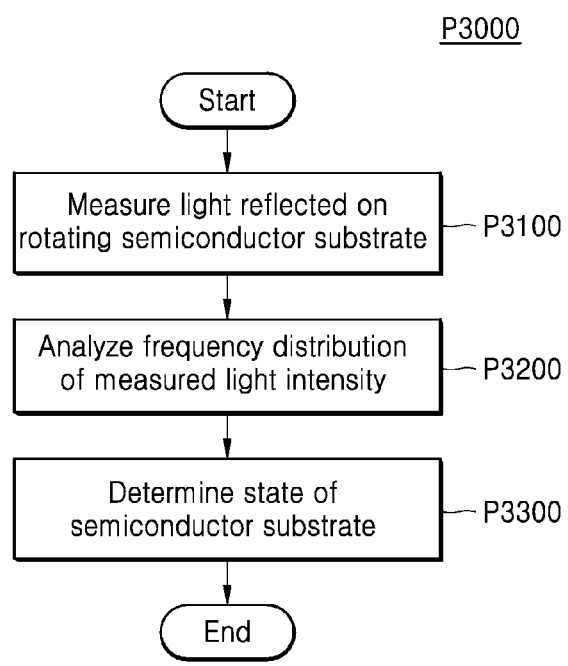
FIG. 3 is a flowchart of a method of inspecting a semiconductor substrate, according to some exemplary embodiments.

FIG. 3 is a flowchart of a method of inspecting a state of a semiconductor substrate according to some embodiments.

Referring to FIGS. 1 to 3, a process P3000 of inspecting a state of a semiconductor substrate W may include a process P3100 of measuring light intensity of light reflected on a rotating semiconductor substrate W, a process P3200 of analyzing a frequency distribution of the measured light intensity, and a process P3300 of determining the state of the semiconductor substrate W based on the analysed frequency distribution of the measured light intensity.

In process P3100, an optical sensor 210 may be irradiated with light emitted by a lamp 120 and may measure light intensity of light reflected on the semiconductor substrate W. For example, as the semiconductor substrate W rotates, the optical sensor 210 may receive information about the light intensity of light reflected on the semiconductor substrate W during the rotation. According to some embodiments, a state of the semiconductor substrate W may be inspected by using light generated by the lamp 120 corresponding to a thermal light source, without using a separate light source for measurements.

In process P3200, the frequency converter 260 may perform frequency analysis on data about the light intensity measured by the optical sensor 210 in process P3100. According to some embodiments, the frequency converter 260 may determine a magnitude of a frequency component corresponding to a specific frequency at each time point. Here, the magnitude of the frequency component may be a magnitude of light intensity corresponding to a specific frequency in a light intensity frequency distribution, which is calculated by performing a Fourier transform on measurement data about the light intensity.

Thereafter, in process P3300, a state of the semiconductor substrate W may be determined as will be described with reference to FIGS. 4A to 5C.

Figure 4A:
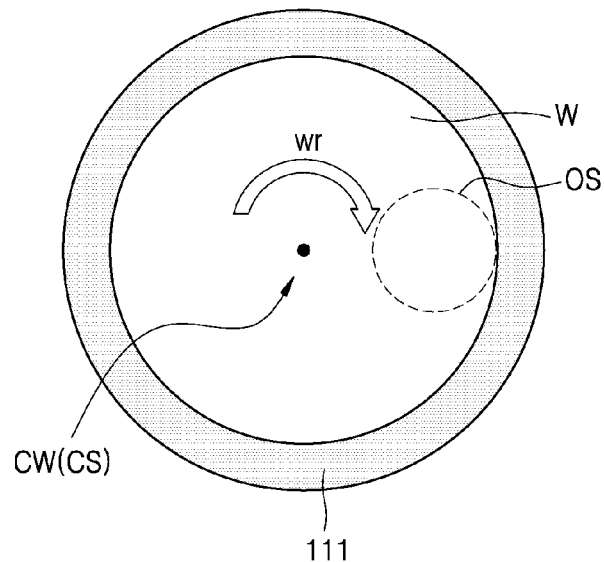
FIGS. 4A to 4C are plan views of a method of inspecting a semiconductor substrate, according to some exemplary embodiments.
Figure 4B:
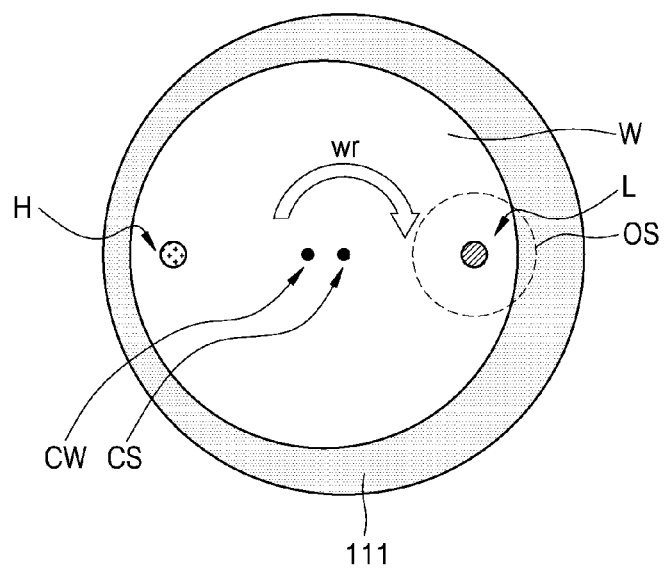
Figure 4C:
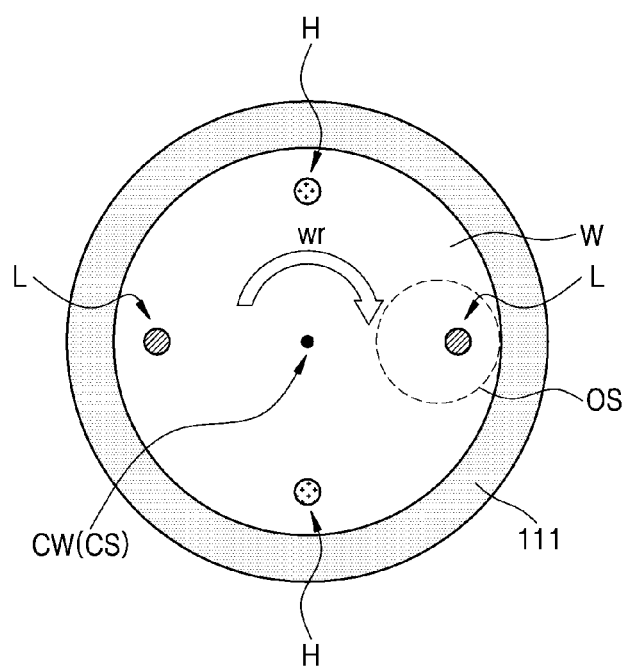
Figure 5A:
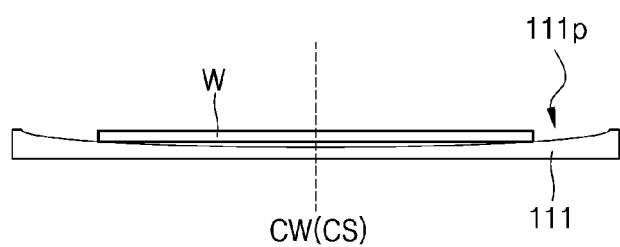
FIGS. 5A to 5C are side sectional views of a method of inspecting a semiconductor substrate, according to some exemplary embodiments.
Figure 5B:
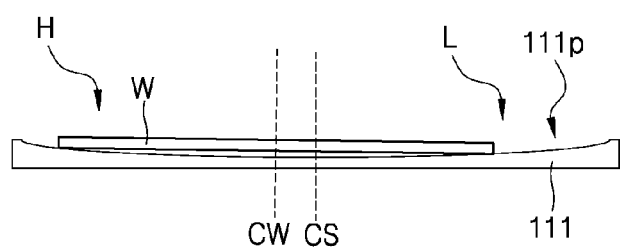
Figure 5C:
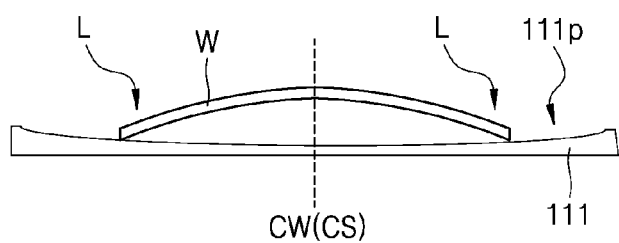

FIGS. 4A to 4C are plan views of a method of determining a state of a semiconductor substrate W from an analysis of light intensity of light reflected on the rotating semiconductor substrate W, and FIGS. 5A to 5C are cross-sectional views corresponding respectively to FIGS. 4A to 4C.

FIGS. 4A and 5A illustrate an embodiment in which the semiconductor substrate W may be normally disposed on a substrate support unit 111 of a susceptor (e.g., susceptor 110 in FIG. 1). In FIGS. 4A to 5C, components of a process chamber other than the semiconductor substrate W and the substrate support unit 111 will be omitted for brevity.

Herein, an observation region OS may refer to a region of the semiconductor substrate W, which is condensed or concentrated by an optical fiber OF and inspected by an optical sensor 210. A substrate central axis CW may be an axis of the semiconductor substrate W that is perpendicular to a top surface of the semiconductor substrate W and passes through the center of the semiconductor substrate W. A susceptor central axis CS may be an axis of the susceptor 110 that is perpendicular to the top surface of the semiconductor substrate W and passes through the center of the susceptor 110 and the substrate support unit 111. When the semiconductor substrate W is normally disposed on the substrate support unit 111, the susceptor central axis CS may substantially coincide with the substrate central axis CW. As shown in FIGS. 4A-4C, a curved arrow is used to indicate that the semiconductor substrate W rotates about the susceptor central axis CS, and a rotational angular velocity 'wr' refers to an angular velocity at which the semiconductor substrate W rotates. The rotational angular velocity 'wr' may be set to an appropriate velocity based on the processing of the semiconductor substrate W. Here, the rotational angular velocity 'wr' may have a relationship with a rotation frequency 'fr' as shown in Equation 1:

$$fr = \frac{wr}{2\pi},\qquad\text{EQUATION 1}$$

wherein π may denote a circumferential rate, and the rotational angular velocity 'wr' and the rotation frequency 'fr' may be regarded as substantially equivalent concepts. Accordingly, the description of the rotational angular velocity 'wr' in the present specification may be applied to the rotation frequency 'fr' in a similar manner, and vice versa.

Since the semiconductor substrate W, while in a normal state, has rotational symmetry to the substrate central axis CW, when the semiconductor substrate W rotates about the substrate central axis CW, it may not be determined whether the semiconductor substrate W rotates. Thus, data about the magnitude of the light intensity of light reflected on the top surface of the semiconductor substrate W, which is measured by the optical sensor 210, may not include information about the rotation of the semiconductor substrate W.

FIGS. 4B and 5B illustrate an embodiment in which the semiconductor substrate W may be misaligned with or inclined with respect to the substrate support unit 111. Misalignment or inclination may occur before and/or after a process. Although FIG. 4B illustrates a case in which the misalignment and the inclination of the semiconductor substrate W with respect to the substrate support unit 111 occur simultaneously, the inventive concept is not limited thereto, and only one of the misalignment and the inclination may occur.

According to some embodiments, when the semiconductor substrate W is misaligned with the substrate support unit 111, the substrate central axis CW and the susceptor central axis CS may be spaced apart from each other in a lateral direction (e.g., in the X- and/or Y-direction). According to some embodiments, the semiconductor substrate W may rotate by using the susceptor central axis CS as a rotation axis. When the substrate central axis CW and the susceptor central axis CS are spaced apart from each other, as illustrated in FIGS. 4B and 5B, the rotation symmetry of the semiconductor substrate W may be broken and the semiconductor substrate W may be considered to be misaligned. For example, the misaligned semiconductor substrate W may rotate assymetrically around the susceptor central axis CS. As the misaligned semiconductor substrate W rotates around the susceptor central axis CS, a width of the semiconductor substrate W, included in the observation region OS, may vary. Thus, data about light intensity of light reflected on the misaligned semiconductor substrate W may include information about the rotation of the semiconductor substrate W. Specifically, the data may include a time point at which the width of the semiconductor substrate W, included in the observation region OS, is largest and a time point at which the width is smallest during a single rotation of the semiconductor substrate W According to some embodiments, when data about light intensity of light reflected on the misaligned semiconductor substrate W is analyzed through a Fourier transform, a frequency component that is substantially equal to the rotation speed of the semiconductor substrate W may be measured to have a relatively high value.

According to some embodiments, when the top surface of the semiconductor substrate W is inclined with respect to the substrate support unit 111, since the substrate central axis CW is inclined with respect to the susceptor central axis CS, the rotation symmetry of the semiconductor substrate W may be broken. According to some embodiments, since the semiconductor substrate W rotates while being inclined with respect to the substrate support unit 111, a path and angle of light that is reflected on the top surface of the semiconductor substrate W and that reaches the optical sensor 210 may vary. Thus, data about the light intensity of light reflected on the inclined semiconductor substrate W may include information about the rotation of the semiconductor substrate W. Specifically, during a single rotation of the inclined semiconductor substrate W, each of a high portion H and a low portion L of the top surface of the semiconductor substrate W may be included once in the observation region OS. According to some embodiments, when data about light intensity of light reflected on the inclined semiconductor substrate W is analyzed through a Fourier transform, a frequency component that is substantially equal to the rotation speed of the semiconductor substrate W may be measured to have a relatively high value.

FIGS. 4C and 5C illustrate an embodiment in which warpage of the semiconductor substrate W may occur. When warpage occurs, the semiconductor substrate W may not be considered to be normally disposed. The warpage of the semiconductor substrate W may occur due to stress imbalance caused by differences in coefficient of thermal expansion (CTE) among respective portions of the semiconductor substrate W. According to some embodiments, the semiconductor substrate W may be aligned with the substrate support unit 111. The substrate central axis CW may substantially coincide with the susceptor central axis CS. For example, in the embodiment of FIGS. 4C and 5C, the semiconductor substrate W may not be considered to be misaligned or inclined, but may be considered to be warped.

According to some embodiments, as the semiconductor substrate W warps, a high portion H and a low portion L may be caused in the semiconductor substrate W. Although FIGS. 4C and 5C illustrate a case in which two high portions H and two low portions L are caused, the inventive concept is not limited thereto. According to some embodiments, even if misalignment or inclination is not caused in the semiconductor substrate W, the rotation symmetry of the warped semiconductor substrate W may be broken.

Specifically, during a single rotation of the warped semiconductor substrate W, each of a high portion H and a low portion L may be included in the observation region OS twice at the top surface of the semiconductor substrate W. According to some embodiments, when data about light intensity of light reflected on the semiconductor substrate W is analyzed through a Fourier transform, a frequency component that is substantially equal to twice the rotation speed of the warped semiconductor substrate W may be measured to have a relatively high value.

To sum up the descriptions of FIGS. 4A to 5C, when the semiconductor substrate W is normally disposed, in data obtained by performing a Fourier transform on the light intensity of light reflected on the semiconductor substrate W, a direct-current (DC) component corresponding to a frequency of 0 Hz may have a relatively high value. When the semiconductor substrate W is abnormally disposed, harmonics corresponding to the rotation frequency 'fr' and an integer multiple thereof may have a relatively high value. When the semiconductor substrate W is inclined or misaligned with respect to the substrate support unit 111, in the data obtained by performing a Fourier transform on the light intensity of light reflected on the semiconductor substrate W, a first harmonics component that is substantially equivalent to the rotation frequency 'fr' may have a relatively high value. When warpage occurs in the semiconductor substrate W, in the data obtained by performing a Fourier transform on the light intensity of light reflected on the semiconductor substrate W, a second harmonics component that is substantially equivalent to twice the rotation frequency 'fr' may have a relatively high value. The inclination, misalignment, and warpage of the semiconductor substrate W, which are described with reference to FIGS. 4B and 5B and FIGS. 4C and 5C, may simultaneously occur according to circumferences. Alternatively, only one or two of the inclination, misalignment, and warpage of the semiconductor substrate W may occur.

In P3300, in the data about the light intensity of light reflected on the semiconductor substrate W, when the first harmonics component for the rotation frequency 'fr' is detected to be a relatively high value, it may be determined that a misalignment or an inclination has occurred in the semiconductor substrate W. In the data about the light intensity of light reflected on the semiconductor substrate W, when the second harmonics component for the rotation frequency 'fr' is detected to be a relatively high value, it may be determined that warpage has occurred in the semiconductor substrate W. The determination of thicknesses of films deposited on the semiconductor substrate W and dimensions of patterns based on light intensity of light reflected on the semiconductor substrate W will be described below.

Figure 6:
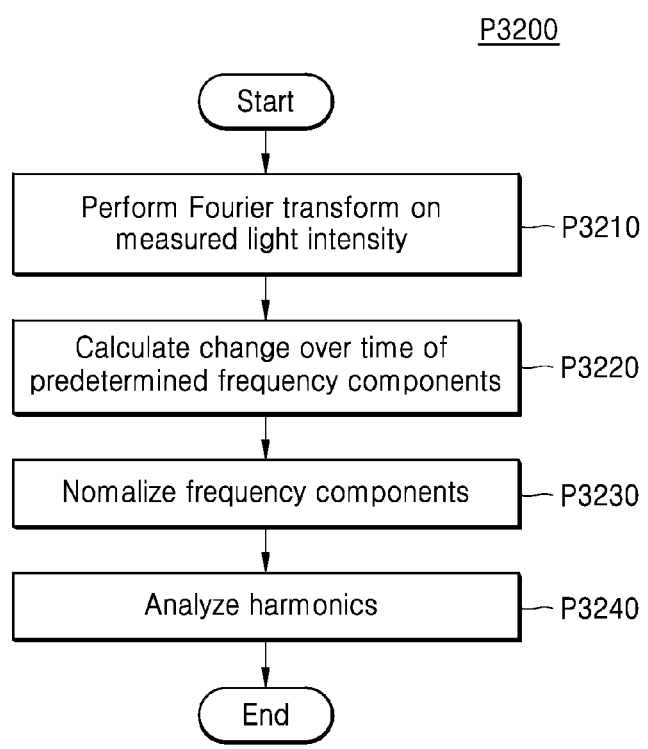
FIG. 6 is a flowchart of a process of analyzing frequency characteristics of light intensity of light reflected on a semiconductor substrate W, according to some exemplary embodiments.

FIG. 6 is a flowchart of a process of analyzing frequency characteristics of light intensity of light reflected on a semiconductor substrate W.

Figure 7:
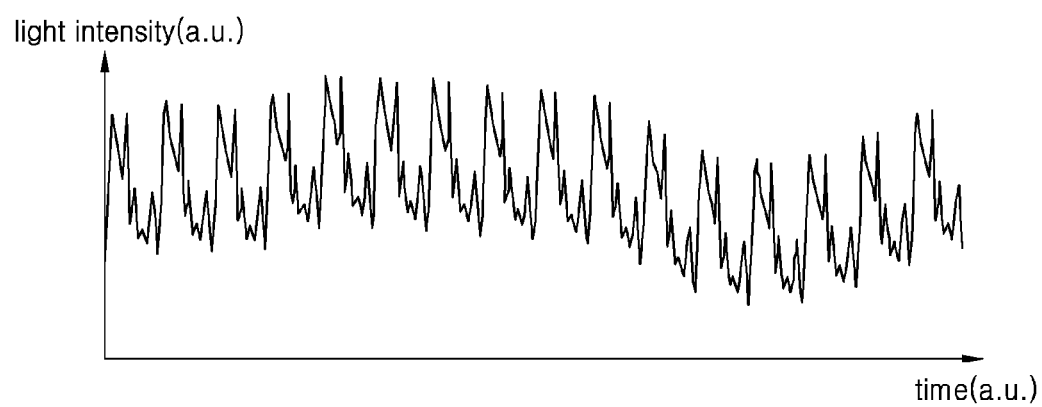
FIGS. 7 to 14 are graphs showing a method of inspecting a semiconductor substrate, according to some exemplary embodiments.
Figure 8:
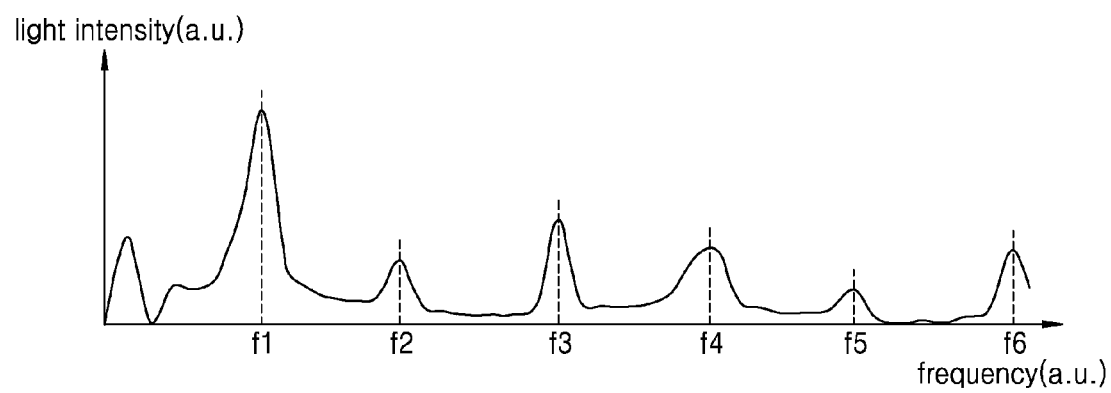

FIG. 7 is a graph showing a variation in light intensity of light reflected on a semiconductor substrate W with respect to time. FIG. 8 is a graph showing analysis results of a frequency distribution of light intensity of FIG. 7 at a specific time point by using a method of analyzing a frequency, which will be described below.

Referring to FIGS. 1 and 6 to 8, in process P3210, the frequency converter 260 may perform a Fourier transform on data about light intensity of light reflected on the semiconductor substrate W, which is measured by the optical sensor 210. According to some embodiments, the frequency converter 260 may perform frequency analysis on data about light intensity by using a Fourier transform for a finite time period.

Frequency conversion of the frequency converter 260 at a specific time point 't' may be explained by Equation 2:

$$I(f, t) = \int_{t-T}^{t} i(\tau) e^{j 2 \pi f \tau} d\tau, \qquad \text{EQUATION 2:}$$

wherein T may denote a predetermined time interval, which may be determined based on process conditions and on-line/off-line data. 'e' may denote a Euler constant, 'j' may denote a unit imaginary number, $\pi$ may denote a circumferential rate, $\tau$ may denote a time variable, and 'f' may denote a frequency. I(f, t) may denote a light intensity function of a frequency domain at a time point 't', and a magnitude of the light intensity function in the frequency domain may vary according to frequency and time. i($\pi$) may denote a light intensity function in a time domain, and a magnitude of the light intensity function in the time domain may vary according to time.

Referring to FIGS. 7 and 8, the light intensity function i($\pi$) in the time domain may vary according to the rotation of the semiconductor substrate W and intensity of a lamp itself. FIG. 8 shows a frequency distribution of light intensity at a specific time point. From FIG. 8, it can be confirmed that harmonics for first to sixth frequencies f1, f2, f3, f4, f5, and f6, which are a first frequency f1 and two to six multiples thereof, reached peaks of the light intensity distribution. Here, the first frequency f1 may be substantially equal to the rotation frequency 'fr'.

Figure 9A:
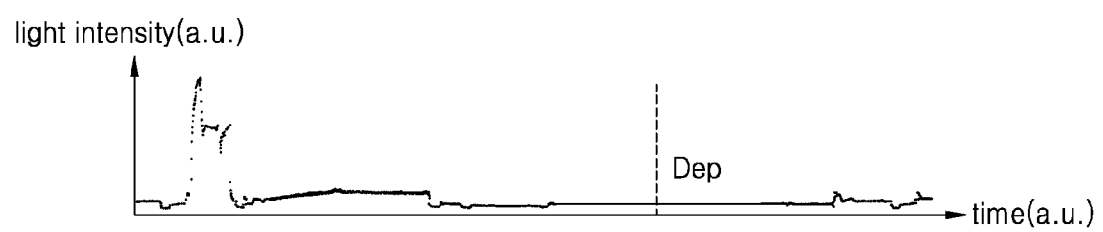
Figure 9B:
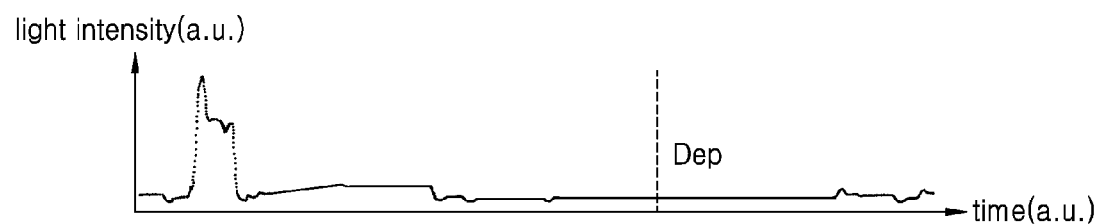
Figure 9C:
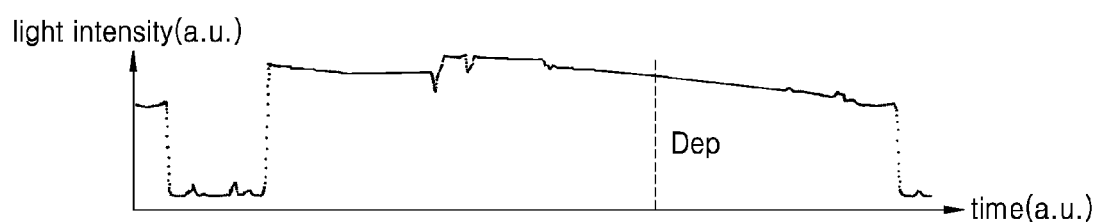
Figure 9D:
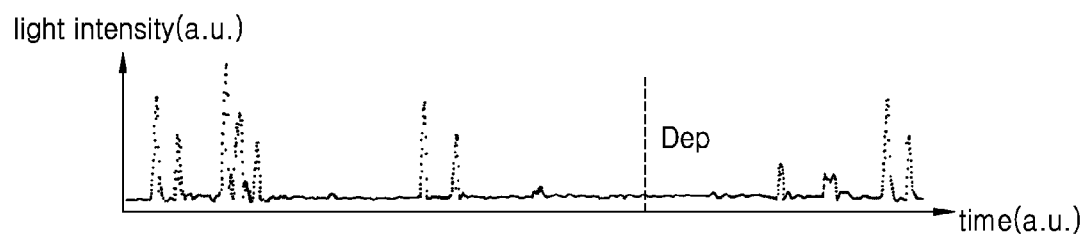

FIG. 9A is a graph showing light intensity of light reflected on a semiconductor substrate W with respect to time. FIG. 9B is a graph showing a magnitude of a DC component with respect to time, wherein the DC component has a frequency of 0 Hz, from among the light intensity of FIG. 9A. The graph of FIG. 9B may correspond to embodiments in which the semiconductor substrate W is normally disposed, such as discussed above in connection with FIGS. 4A and 5A. FIG. 9C is a graph showing a magnitude of a first frequency component with respect to time, wherein the first frequency component has a first frequency f1 substantially equal to a rotation frequency 'fr', from among the light intensity of FIG. 9A. The graph of FIG. 9C may correspond to embodiments in which the semiconductor substrate W is abnormally disposed due to misalignment or inclination, such as discussed above in connection with FIGS. 4B and 5B. FIG. 9D is a graph showing a magnitude of a second frequency component with respect to time, wherein the second frequency component has a second frequency f2 substantially equal to twice the rotation frequency 'fr', from among the light intensity of FIG. 9A. The graph of FIG. 9D may correspond to embodiments in which the semiconductor substrate W is abnormally disposed due to warpage, such as discussed above in connection with FIGS. 4C and 5C.

FIGS. 9B to 9D illustrate a case in which only the DC component, the first frequency component, and the second frequency component are extracted from the measured light intensity, but the inventive concept is not limited thereto. Harmonics equal to or higher than third harmonics for the first frequency f1 and a frequency component distributed between the respective harmonics may be extracted from the measured light intensity.

Referring to FIGS. 6 and 9A to 9D, in process P3220, the frequency analyzer 270 may calculate a variation in magnitude of light intensity corresponding to a specific frequency with respect to time, based on the frequency distribution obtained in process P3210.

A deposition start point 'dep' is illustrated in each of FIGS. 9A to 9D. When predetermined films are deposited on the semiconductor substrate (e.g., semiconductor substrate W in FIG. 1), since rigidity or internal stress of the semiconductor substrate W is reinforced, warpage of the semiconductor substrate W may be reduced. Accordingly, when the predetermined films are deposited on the semiconductor substrate (e.g., semiconductor substrate W in FIG. 1), a magnitude of a second harmonics component, from among the light intensity of light reflected on the semiconductor substrate W, may be reduced. In this case, light intensity of light emitted by the lamp (e.g., lamp 120 in FIG. 1) may be changed over time to adjust a temperature of the process chamber (e.g., process chamber 100 in FIG. 1). For example, the process controller 150 may increase the light intensity of the light emitted by the lamp 120 to increase the temperature of the process chamber 100 or the process controller 150 may decrease the light intensity of the light emitted by the lamp 120 to decrease the temperature of the process chamber 100. A variation in the magnitude of the light intensity of light emitted by the lamp 120 may affect the entire light intensity and the respective frequency components. Referring to FIGS. 9A to 9D, the light intensity, the DC component, the first frequency component, and the second frequency component, which are reflected on the semiconductor substrate W, may not have a special aspect to determine the deposition start point 'dep'.

FIGS. 10A to 10D are graphs showing values obtained by sequentially normalizing the results of FIGS. 9A to 9D, respectively.

Referring to FIGS. 6 and 10A to 10D, a variation of a magnitude of each frequency component with respect to time, which is determined in process P3220, may be normalized in process P3230. According to some embodiments, the frequency analyzer 270 may normalize the first frequency component and the second frequency component by using a DC component. According to some embodiments, the frequency analyzer 270 may divide the first frequency component from the second frequency component by using the DC component and may normalize the first frequency component and the second frequency component. According to some embodiments, at every time point, the frequency analyzer 270 may divide the first frequency component from the second frequency component by using the DC component and may calculate time variations of the normalized first and second frequency components.

Figure 10A:
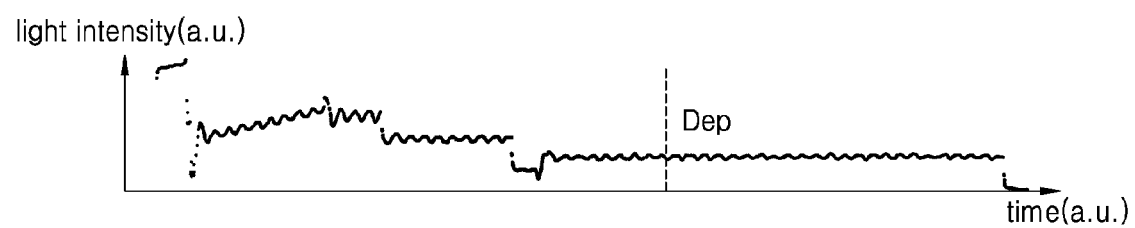
Figure 10B:
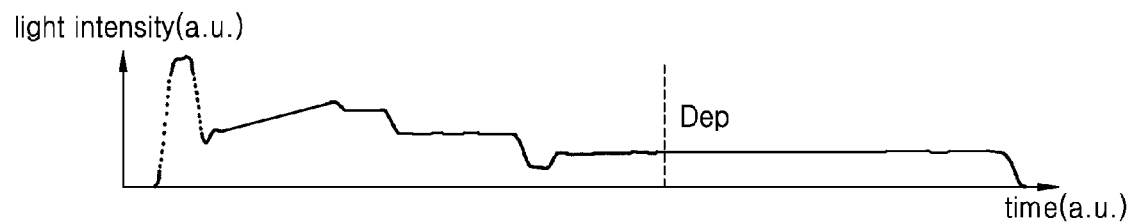
Figure 10C:
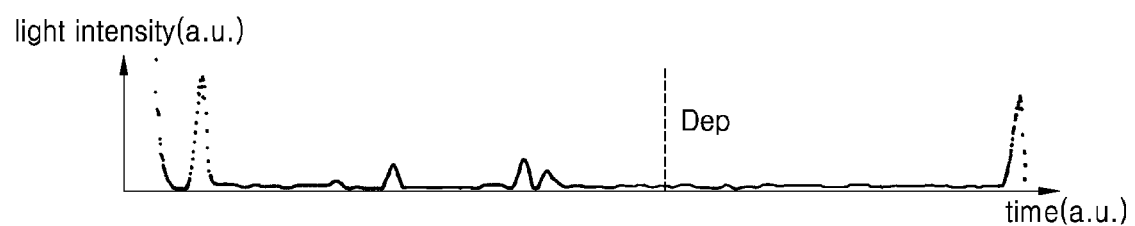
Figure 10D:
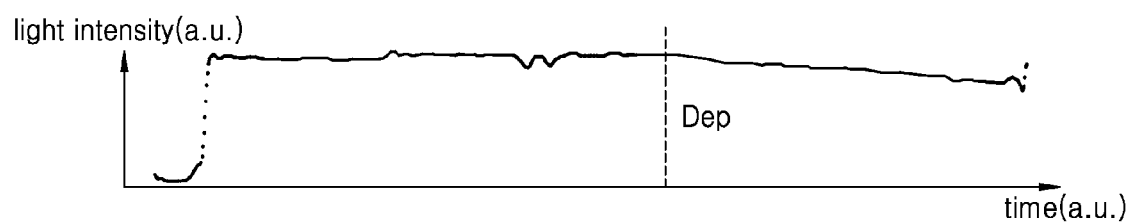

In the Fourier transform, each of frequency components other than the DC component may correspond to a trigonometric function, and the average value of each of the frequency components during one period may be substantially 0. Thus, the average value of the total light intensity at each time point may be substantially equal to a value of the DC component. According to some embodiments, by dividing each of the harmonics components by the DC component, a variation in each of the frequency components relative to the light intensity of the lamp (e.g., lamp 120 in FIG. 1) itself may be compensated. Thus, a state of the semiconductor substrate W may be inspected in real-time even in an environment where light intensity in the process chamber 100 is changed over time during the processing of the semiconductor substrate W. Referring to FIG. 10D, it can be seen that after the deposition start point 'dep', the second harmonics component begins to be reduced with time. According to some embodiments, it may be determined whether the warpage of the semiconductor substrate W occurs and an extent of the warpage of the semiconductor substrate W by using the magnitude of the normalized second harmonics component.

Thereafter, in process P3240, harmonics components of the rotation frequency 'fr' may be analyzed. As described above, according to some embodiments, an inclination of the semiconductor substrate W and/or a misalignment of the semiconductor substrate W may be determined from first harmonics of the rotation frequency 'fr' in a light-intensity frequency distribution. For example, referring to FIG. 10C, based on the magnitude of the normalized first harmonics component, it may be determined whether the semiconductor substrate W is inclined or misaligned, and the amounts of inclination or misalignment.

According to some embodiments, warpage of the semiconductor substrate W may be determined from second harmonics of the rotation frequency 'fr' in the light-intensity frequency distribution. For example, based on the magnitude of the normalized second harmonics component, it may be determined whether the semiconductor substrate W is warped. Also, as described below with reference to FIG. 13, according to some embodiments, thicknesses of films deposited on the semiconductor substrate W may be determined from a DC component in the light-intensity frequency distribution. Furthermore, as described below with reference to FIG. 14, according to some embodiments, a CD of a pattern may be determined from the DC component and the second harmonics component in the light-intensity frequency distribution.

Figure 11A:
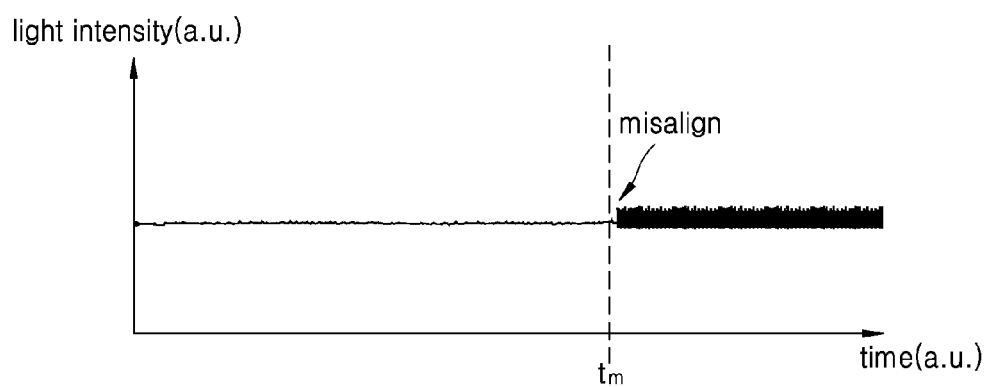
Figure 11B:
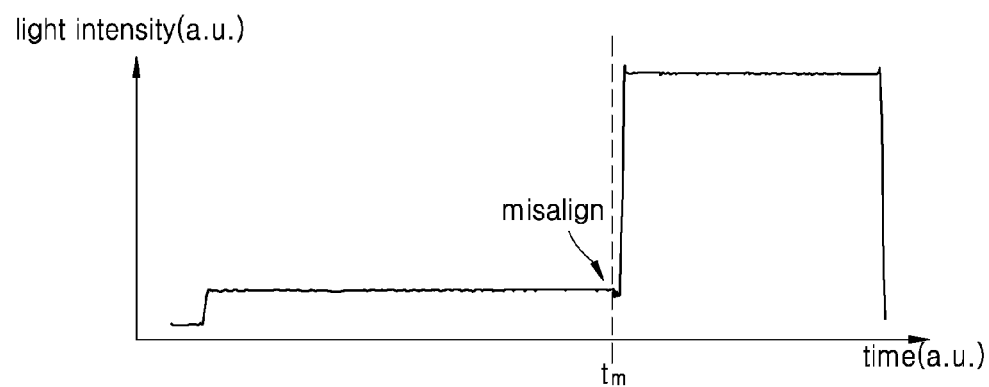

FIG. 11A is a graph showing light intensity of light reflected on a semiconductor substrate W with respect to time in an experimental example. FIG. 11B is a graph showing a variation in first harmonics component of FIG. 11A with respect to time.

Referring to FIGS. 1, 11A, and 11B, the semiconductor substrate W was intentionally misaligned with the susceptor 110 at a misalignment time 'tm'. From FIG. 11B, it may be confirmed that the magnitude of the first harmonics component greatly increased directly after the misalignment. Although the experimental example of FIGS. 11A and 11B are performed with respect to misalignment, similar results would result from inclination of the semiconductor substrate W with respect to the susceptor 110. According to some embodiments, it may be determined whether the misalignment and/or inclination of the semiconductor substrate W occur and extents of the misalignment and/or inclination of the semiconductor substrate W by using the magnitude of the normalized first harmonics component and a variation thereof.

Figure 12:
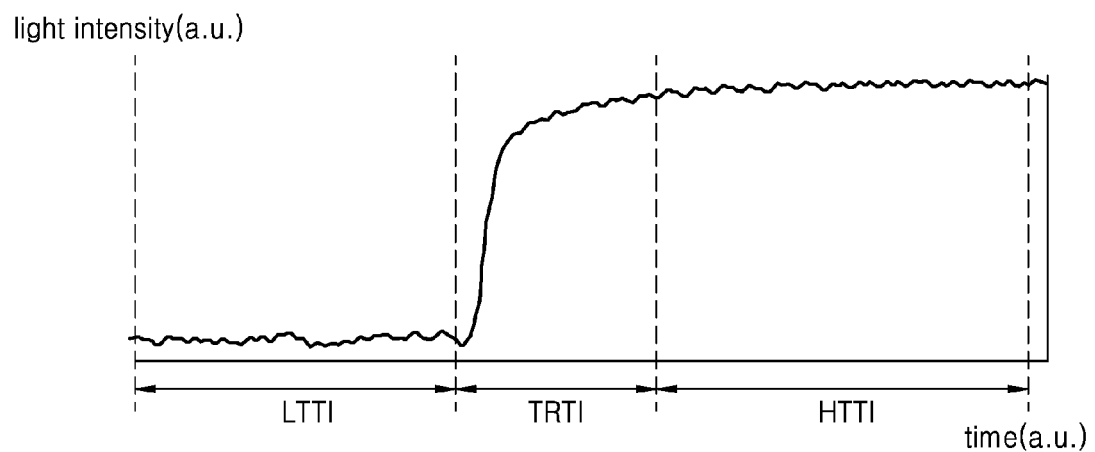

FIG. 12 is a graph showing a magnitude of a second harmonics component, from among light intensity of light reflected on a semiconductor substrate W, with respect to time in an experimental example.

Referring to FIGS. 1 and 12, a process chamber 100 into which the semiconductor substrate W is loaded may sequentially undergo a low-temperature interval LTTI in which the process chamber 100 maintains a constant low temperature, a temperature-rise interval TRTI in which a temperature of the process chamber 100 rises, and a high-temperature interval HTTI in which the process chamber 100 maintains a constant high temperature. Referring to FIG. 12, it may be confirmed that the magnitude of the second harmonics component varies with a variation in the temperature of the process chamber 100. And as the temperature of the process chamber 100 rises, the warpage of the semiconductor substrate W may increase and the magnitude of the second harmonics component may also increase. From the present experimental example, it may be determined whether the warpage of the semiconductor substrate W occurs and an extent of the warpage of the semiconductor substrate W by using the magnitude of the normalized second harmonics component.

Figure 13:
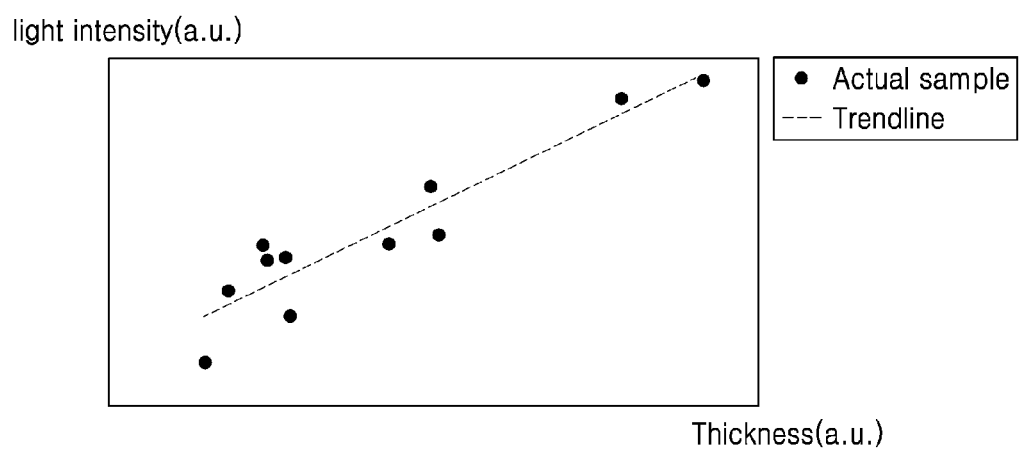

FIG. 13 is a graph showing a correlation between a magnitude of a DC component of light intensity of light reflected on a semiconductor substrate and thicknesses of films deposited on the semiconductor substrate in some experimental examples.

Referring to FIGS. 1 and 13, filled circles indicate light intensities of light reflected on a measured semiconductor substrate W relative to thicknesses of predetermined films deposited on the semiconductor substrate W, and a dashed line indicates a trendline of the circles. In this case, an R-square coefficient of determination ($R^2$) may be about 0.8758. Here, the R-square coefficient of determination indicates an extent to which a portion SSR described by a regression line occupies in the total variance SST and may be defined by $R^2$=SSR/SST. For example, the R-square coefficient of determination may be the ratio of the predicted variance SSR to the total variance SST. The R-square coefficient of determination may be a measure of how accurately an equation of the regression line describes original data. The closer the R-square coefficient of determination becomes to 1, the more accurately the equation of the regression line describes the original materials. Accordingly, the value $R^2$ (=0.8758) may indicate that the DC component accurately describes the thicknesses of predetermined films deposited on the semiconductor substrate W.

According to some embodiments, a thickness of a film deposited on the semiconductor substrate W may be determined by using a predetermined function on a value of the DC component. According to some embodiments, the thickness of the film deposited on the semiconductor substrate W may be determined by using a predetermined linear function on the value of the DC component. According to some embodiments, the determination of the thickness of the film deposited on the semiconductor substrate W by using the value of the DC component may include determining coefficients of a linear function of a DC component of the thickness of the film deposited on the semiconductor substrate W. The determination of the thickness of the film deposited on the semiconductor substrate W, which is described above with reference to FIG. 13, may be included in the process P3300 described with reference to FIG. 3.

Figure 14:
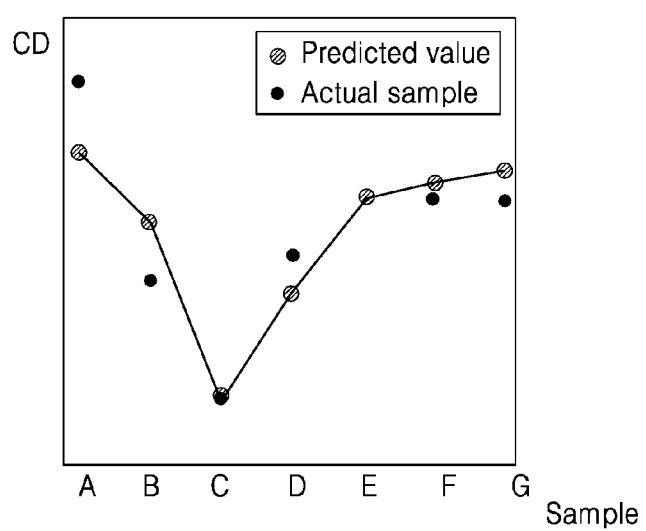

FIG. 14 is a graph showing calculation results and actually measured values of frequency components of light intensity of light reflected on a rotating semiconductor substrate in some experimental examples (Samples A to G).

Referring to FIGS. 1 and 14, according to some embodiments, a pattern may be formed by etching the predetermined layers formed on the semiconductor substrate W, and additional films may be stacked on the pattern. According to some embodiments, a CD of the pattern may be calculated based on thicknesses of the additionally stacked films and a width of the etched pattern.

According to Roark and Young's formulas for deformation of discs, deformation of the semiconductor substrate W is inversely proportional to the cube of a thickness of the semiconductor substrate W and is proportional to a load acting on the semiconductor substrate W. According to some embodiments, since the load acting on the semiconductor substrate W corresponds to a thickness of a deposited film, the load acting on the semiconductor substrate W may be obtained by a DC component, and warpage of the semiconductor substrate W may be obtained by using a second harmonics component. According to some embodiments, a CD of a pattern may be obtained by performing a predetermined calculation on the DC component and the second harmonics component.

The process of obtaining the CD of the pattern formed on the semiconductor substrate, which is described with reference to FIG. 14, may be included in process P3300 of FIG. 3.

While the processing of the semiconductor substrate W, when the semiconductor substrate W is mounted on a susceptor, the semiconductor substrate W may be misaligned with or inclined with respect to a substrate pocket. Alternatively, after the semiconductor substrate W is loaded into a chamber, the semiconductor substrate W may move relatively to the susceptor during a process and become misaligned with the substrate pocket or inclined with respect to the susceptor. In addition, the warpage or inclination of the semiconductor substrate W may occur due to a rise in temperature of the semiconductor substrate W and a difference in CTE between portions of the semiconductor substrate W. These problems, such as the misalignment, the inclination, and the warpage, may cause failures to the semiconductor substrate W during subsequent processes. Accordingly, the misalignment, the inclination, and the warpage may need to be adjusted to return the calculated values to predetermined reference values or lower.

A wafer inspection device of the related art collected signals using an additional laser light source and directly measured a degree of warpage to determine a state of a wafer. In an environment where a temperature of the process chamber 100 is controlled by a thermal light source, such as the lamp 120, a magnitude of light intensity of light emitted by the lamp 120 may be much higher than that of light intensity of light emitted by a laser light source, so that it may be substantially impossible to measure displacement of a substrate using an additional laser light source.

In a method of manufacturing a semiconductor device according to some embodiments, it may be inspected in real-time to determine whether there are problems, such as misalignment, inclination, and warpage, even in an environment using a thermal light source (e.g., the lamp 120), so that a process environment of a semiconductor substrate to which the problems are caused may be reset. Furthermore, in the method of manufacturing the semiconductor device according to some embodiments, thicknesses of films deposited on a semiconductor substrate may be calculated in real-time, and a CD of a pattern formed on the semiconductor substrate may be measured. Thus, the reliability of the state of the semiconductor substrate and the processing of the semiconductor substrate may be enhanced.

While the inventive concept has been particularly shown and described with reference to embodiments, thereof, it will be understood that various changes in form and details may be made therein without departing from the spirit and scope of the following claims.

What is claimed is:

1. A method of inspecting a semiconductor substrate, the method comprising:
    measuring light intensity of light reflected on the semiconductor substrate while the semiconductor substrate rotates;
    analyzing a frequency distribution of the measured light intensity; and
    determining a state of the semiconductor substrate based on the frequency distribution,
    wherein the analyzing of the frequency distribution of the measured light intensity comprises extracting a plurality of frequency components corresponding respectively to a plurality of frequencies from the measured light intensity, and
    wherein the analyzing of the frequency distribution of the measured light intensity comprises extracting from the measured light intensity a direct-current (DC) component corresponding to a frequency of 0 Hz, a first frequency component corresponding to a first frequency, and a second frequency component corresponding to a second frequency, which is twice the first frequency.

2. The method of claim 1,
    wherein the semiconductor substrate comprises at least one film deposited on the semiconductor substrate, and
    wherein the determining of the state of the semiconductor substrate comprises determining a deposited thickness of the at least one film by using the DC component.

3. The method of claim 1, wherein the first frequency is substantially equal to a frequency at which the semiconductor substrate rotates.

4. The method of claim 3,
    wherein the semiconductor substrate is located on a susceptor configured to contain and rotate the semiconductor substrate, and
    wherein the determining of the state of the semiconductor substrate comprises determining misalignment of the semiconductor substrate with the susceptor by using the first frequency component.

5. The method of claim 3,
    wherein the semiconductor substrate is located on a susceptor capable of containing and rotating the semiconductor substrate, and
    wherein the determining of the state of the semiconductor substrate comprises determining inclination of the semiconductor substrate with respect to the susceptor by using the first frequency component.

6. The method of claim 3, wherein the determining of the state of the semiconductor substrate comprises determining warpage of the semiconductor substrate by using the second frequency component.

7. The method of claim 3,
    wherein the semiconductor substrate is located on a susceptor capable of receiving the semiconductor substrate, and at least one concavo-convex pattern is formed on the semiconductor substrate, and
    wherein the determining of the state of the semiconductor substrate by using the frequency distribution of the light intensity comprises determining a critical dimension (CD) of the at least one concavo-convex pattern by using the DC component and the second frequency component.

8. The method of claim 1, wherein the analyzing of the frequency distribution of the measured light intensity comprises normalizing the frequency distribution of the measured light intensity.

9. The method of claim 1, wherein the analyzing the frequency distribution of the measured light intensity is performed by performing a Fourier transform for a predetermined time interval.

10. A method of inspecting a semiconductor substrate, the method comprising:
    measuring light intensity of light reflected on the semiconductor substrate while the semiconductor substrate rotates;
    analyzing a frequency distribution of the measured light intensity; and
    determining a state of the semiconductor substrate based on the frequency distribution of the light intensity,
    wherein the analyzing of the frequency distribution of the light intensity comprises normalizing the frequency distribution of the light intensity, and
    wherein the normalizing of the frequency distribution of the light intensity comprises extracting from the measured light intensity a direct-current (DC) component corresponding to a frequency of 0 Hz, a first frequency component corresponding to a first frequency, and a second frequency component corresponding to a second frequency, which is twice the first frequency, and normalizing the first frequency component and the second frequency component by using the DC component.

11. The method of claim 10, wherein the normalizing of the first frequency component and the second frequency component comprises dividing the first frequency component from the second frequency component using the DC component.

12. The method of claim 10, wherein the analyzing of the frequency distribution of the light intensity comprises calculating variations in the DC component and the normalized first and second frequency components with respect to time.

13. The method of claim 10, wherein the first frequency is substantially equal to a frequency at which the semiconductor substrate rotates.

14. A method of manufacturing a semiconductor device, the method comprising:
    setting a processing environment of a semiconductor substrate;
    processing the semiconductor substrate according to the processing environment;
    inspecting the semiconductor substrate in real-time to determine a state of the semiconductor substrate; and
    determining whether the processing of the semiconductor substrate is to be continued based on the determined state of the semiconductor substrate,
    wherein the inspecting the semiconductor substrate in real-time comprises:
        measuring light intensity of light reflected on the semiconductor substrate while the semiconductor substrate rotates;
        calculating a frequency distribution of the measured light intensity; and determining the state of the semiconductor substrate by using the frequency distribution of the light intensity, wherein the calculating of the frequency distribution of the measured light intensity comprises extracting a plurality of frequency components corresponding respectively to a plurality of frequencies from the measured light intensity, and wherein the calculating of the frequency distribution of the measured light intensity comprises extracting from the measured light intensity a direct-current (DC) component corresponding to a frequency of 0 Hz, a first frequency component corresponding to a first frequency, and a second frequency component corresponding to a second frequency, which is twice the first frequency.

15. The method of claim 14, wherein the first frequency is substantially equal to a frequency at which the semiconductor substrate rotates.

16. The method of claim 14, wherein the semiconductor substrate is located in a chamber comprising a lamp configured to heat the chamber and a susceptor configured to contain and rotate the semiconductor substrate, and wherein the light reflected on the semiconductor substrate comprises light that is emitted by the lamp and reflected on the semiconductor substrate.

17. The method of claim 14, wherein the calculating of the frequency distribution of the light intensity comprises normalizing the frequency distribution of the light intensity.

\* \* \* \* \*